US005614486A

United States Patent [19]

Giersch et al.

[11] Patent Number: 5,614,486

[45] Date of Patent: Mar. 25, 1997

[54] CYCLIC DIESTERS AND THEIR USE AS PERFUMING INGREDIENTS

[75] Inventors: Wolfgang K. Giersch, Bernex; Peter Fankhauser, Meyrin, both of Switzerland

[73] Assignee: Firmenich SA, Geneva, Switzerland

[21] Appl. No.: 448,285

[22] Filed: May 23, 1995

[30] Foreign Application Priority Data

Jul. 1, 1994 [CH] Switzerland ............................ 2103/94

[51] Int. Cl.$^6$ ........................................................ A61K 7/46

[52] U.S. Cl. .................................. 512/21; 512/24; 560/1; 560/66; 560/76; 560/126; 560/127

[58] Field of Search .......................... 512/21, 24; 560/66, 560/126, 1, 76, 127, 60

[56] References Cited

U.S. PATENT DOCUMENTS

| | | | |
|---|---|---|---|
| 4,168,248 | 9/1979 | Kulka | 512/21 |
| 4,624,802 | 11/1986 | Schaper et al. | 512/21 |
| 5,066,640 | 11/1991 | Voss et al. | 512/21 |
| 5,112,864 | 5/1992 | Djuric et al. | 514/549 |

FOREIGN PATENT DOCUMENTS

| | | |
|---|---|---|
| 341707 | 11/1989 | European Pat. Off. . |
| 52-136927 | 11/1977 | Japan . |

OTHER PUBLICATIONS

K. Mori et al., "A Mild Transesterification Method", *Synthesis,* Dec., 1993, pp. 790–791.

J. March, "Advanced Organic Chemistry", 3rd Ed., John Wiley & Sons, New York, p. 629, (1985).

R. Imwinkelreid et al., "Diisopropyl (2S,3S)–2,3–O–Isopropylidene Tartrate", Org. Synth., vol. 65, 1987, pp. 230–235.

R. Tabacchi et al., "Contribution to the Knowledge of the Chemical Composition of Oak Moss," Chemical Abstracts, vol. 92, No. 16:135120j (Apr. 21, 1980).

*Primary Examiner*—James H. Reamer

*Attorney, Agent, or Firm*—Pennie & Edmonds

[57] ABSTRACT

The compounds of formula

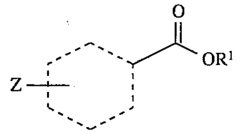

(I)

wherein the Z group can be located in positions ortho-, meta- or para-relative to the carboxylic group, symbol $R^1$ stands for a saturated or unsaturated, linear or branched $C_1$ to $C_4$ alkyl radical and a. the dotted lines represent a cyclohexanic moiety and Z represents a

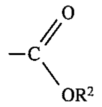

group, $R^2$ being a saturated or unsaturated, linear or branched $C_1$ to $C_4$ alkyl radical; or b. the dotted lines represent a cyclohexanic or benzenic moiety and Z represents a group of formula

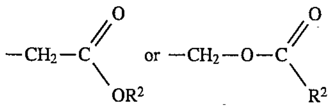

in which $R^2$ is a saturated or unsaturated, linear or branched $C_1$ to $C_4$ alkyl radical, are useful as perfuming ingredients for the preparation of perfuming compositions and a variety of perfumed consumer articles. They impart to the latter odor notes of the fruity and floral type.

5 Claims, No Drawings

CYCLIC DIESTERS AND THEIR USE AS PERFUMING INGREDIENTS

BRIEF SUMMARY OF THE INVENTION

The invention relates to the perfume industry and more particularly to a perfuming composition or a perfumed article which contains as an active perfuming ingredient a compound of formula

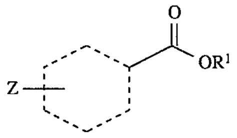

(I)

wherein the Z group can be located in positions ortho-, meta- or para-relative to the carboxylic group, symbol $R^1$ stands for a saturated or unsaturated, linear or branched $C_1$ to $C_4$ alkyl radical and a. the dotted lines represent a cyclohexanic moiety and Z represents a

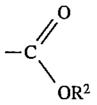

group, $R^2$ being a saturated or unsaturated, linear or branched $C_1$ to $C_4$ alkyl radical; or b. the dotted lines represent a cyclohexanic or benzenic moiety and Z represents a group of formula

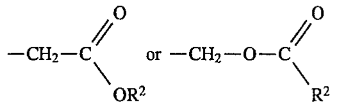

in which $R^2$ is a saturated or unsaturated, linear or branched $C_1$ to $C_4$ alkyl radical.

The invention further provides a perfume or cologne, a soap, a bath or shower gel, a shampoo or other hair-care product, a cosmetic preparation, a body deodorant, an air-freshener, a detergent, a fabric softener or a household product, which contains as a perfuming ingredient a compound of formula (I) as defined above.

The invention also concerns a method to impart, improve, enhance or modify the odor properties of a perfuming composition or of a perfumed article, which method comprises adding to said composition or article a fragrance effective amount of a compound of formula (I) as defined above.

A further object of the invention is a novel compound selected from the group consisting of ethyl 4-(propanoyloxymethyl)-1-cyclohexanecarboxylate and ethyl 4-(propanoyloxy-methyl)-1-benzoate.

BACKGROUND OF THE INVENTION

Amongst the compounds of formula (I) cited above, there are some which are well-known chemical entities. Such is the case for example of the compounds of formula

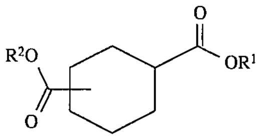

(Ia)

wherein $R^1$ and $R^2$ are identical and represent saturated lower alkyl radicals, which compounds are building blocks of general use polymers.

In spite of the fact that several such compounds have been known for a long while, to the best of our knowledge, there has never been any disclosure of their potential usefulness in the perfuming industry, for preparing perfuming compositions or perfumed products, and it has never even been suggested that they might be potentially interesting as perfuming ingredients.

We have now established that compounds (I) possess surprisingly useful and rare odor notes, with a floral, fruity character of a precious light and ethereal quality, which can nevertheless be accompanied by a good tenacity. In addition, in the best examples, their fruity odor is very natural and not at all of the preserved or crystallized fruit type, nor lactonic, and this renders these compounds particularly precious.

Indeed, in the art of perfumery there is a real demand for light, ethereal, but at the same time tenacious, fruity notes. Amongst the known compounds with these characteristics, it appears that only Fructone® (ethyl 2-methyl-1,3-dioxolane-2-acetate; origin: International Flavors and Fragrances) possesses some tenacity. On the other hand, the only notes known to be both fruity and tenacious are those of an alimentary type, i.e. more reminiscent of the odor of crystallized or stewed fruits, than of the ethereal fruity fragrances emanating from a fresh fruit. Such is the case for example of the fruity lactones, of ethyl methyl phenyl glycidate, or yet of raspberry ketone. The ethereal fruity notes known in the art are those of very volatile esters such as for example hexyl, heptyl and octyl acetates, allyl or ethyl caproate and ethyl butyrate. The present invention provides an advantageous alternative to the latter.

DETAILED DESCRIPTION OF THE INVENTION

We have in fact observed that, unlike the prior known compounds, the chemical entities presently in question can be used to great advantage as a result of their properties mentioned above and best represented in diethyl 1,4-cyclohexanedicarboxylate, the use of which is particularly preferred according to the invention. This compound develops a floral fragrance wherein the fruity character is reminiscent of the odor of pear and strawberry, very ethereal and with a slight pineapple-like bottom note. It is a very natural fresh-fruit note, not at all preserved fruit, nor lactonic, and furthermore of remarkable tenacity for this type of odor. This quality reveals itself both on smelling strip and in the substantive odor of the textiles treated with the detergent and fabric softener compositions which contain the cited carboxylate, as the examples presented further on illustrate.

Another compound of preferred use according to the invention is ethyl 4-(propanoyloxymethyl)-1-cyclohexanecarboxylate, which develops a fruity odor with a slightly woody character, similar to the fruity fragrance of the compound of the invention above-cited.

Although compounds (I) all possess fruity notes, we observed that the quality of the latter could vary considerably from one compound to the next, and even amongst isomers of the same compound. Thus, whereas diethyl 1,3-cyclohexanedicarboxylate possesses an odor similar to that of its 1,4-isomer cited above, diethyl 1,2-cyclohexanedicarboxylate develops a quite distinct fruity note, slightly fatty and reminiscent of the odor of wine lees and carob beans. The use according to the invention of the first of these two compounds in particular is also preferred, as is that of dimethyl 1,2-cyclohexanedicarboxylate, which develops a fruity, ethereal odor recalling that of quince, also slightly minty, while dimethyl 1,3-cyclohexanedicarboxylate possesses a particularly light fruity odor. The fragrances of these two latter compounds do, in fact, contrast with that of dimethyl 1,4-cyclohexanedicarboxylate whose fruity character is more reminiscent of cooked apple.

As a result of their structure, the compounds (I) having a saturated ring can assume two stereoisomeric forms of formula

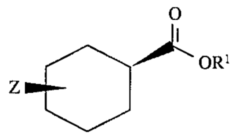

(I') or cis

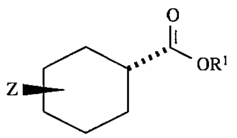

(I")

trans wherein symbols $R^1$ and Z have the meaning indicated in formula (I). It was observed that these two stereoisomers could also present distinct odor properties, which could therefore also differ from those of their mixtures. For example, diethyl cis-1,4-cyclohexanedicarboxylate has a more tenacious and powerful odor than its trans- configuration isomer, with far more body and wherein the typical characters of diethyl 1,4-cyclohexanedicarboxylate are best represented. In a general manner, however, both the stereoisomers, as well as their mixtures, are useful perfuming ingredients.

The cis-configuration isomers, and the mixtures containing a predominant amount thereof, are preferred according to the invention.

Compounds (I), and their cis- or trans-configuration isomers, can be used with equal advantage in both fine and technical perfumery. They are useful for the preparation of a variety of perfuming compositions, bases and concentrates, as well as perfumes and colognes, to which they impart very natural fruity odor characters. Their use for perfuming various consumer products such as soaps, bath and shower gels, shampoos, hair-care creams and lotions, cosmetic preparations or body deodorants, or yet airfresheners, is also advantageous.

In addition, they are also appropriate for perfuming detergents and fabric softeners, as well as household products.

The proportions in Which the compounds according to the invention can be incorporated in the various products abovementioned vary in a wide range of values. The latter depend on the nature of the product to be perfumed and on the desired odor effect, as well as on the nature of the coingredients in a given composition, whenever compounds (I) are used in admixture with current perfuming co-ingredients, solvents or adjuvants. It goes without saying that the compounds according to the invention can also be added to the compositions and perfumed products either on their own, or in solution in the solvents of current use in perfumery.

By way of example, concentrations of the order of 1 to 5%, or even 10% or more by weight of compounds (I), relative to the weight of the composition into which they are incorporated, can be cited. Considerably lower concentrations may nevertheless be quite appropriate when compounds (I) are used to perfume the various consumer products previously cited.

The compounds of formula (I) are either commercial products, or can be easily prepared from commercially available starting products, by way of conventional reactions.

This is in fact another advantage of their use according to the invention, in as much as they are original and economically interesting perfuming ingredients, their industrial synthesis being straightforward and cheap.

A number of known processes can be used for their preparation. For example, since the 1,2-, 1,3- and 1,4-cyclohexanedicarboxylic acids are commercially available compounds (for instance, from Aldrich), compounds (Ia) can be prepared by straightforward esterification of those acids, by means of the appropriate alcohols and in the presence of a protonic acid or an acidic ion exchange resin. These are quite conventional reactions, the conditions of which can be easily optimized by the skilled chemist, without warranting here any further details there-relative.

Alternatively, the compounds (Ia) which possess identical groups $R^1$ and $R^2$ from the dimethyl diesters derived from benzene, which are all available commercially (BASF or HÜLS), via conventional reactions illustrated in the following scheme:

Scheme I

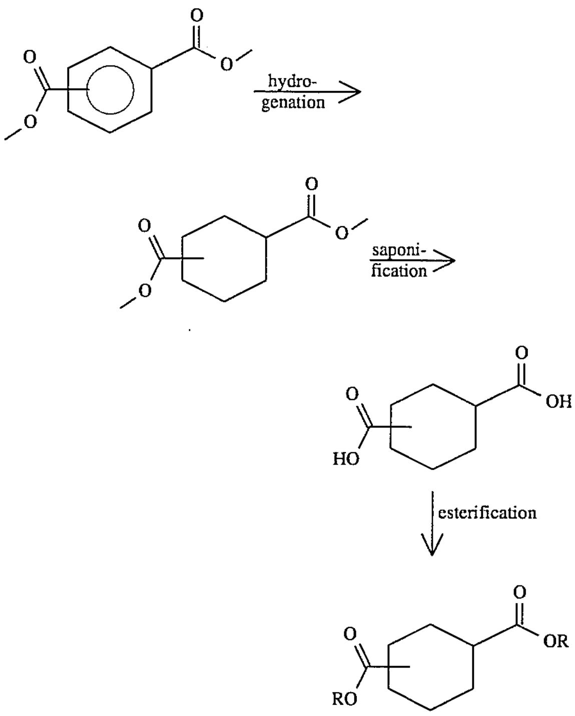

R = $C_2$-$C_4$ alkyl

The reactions represented here-above are carried out under the usual conditions, described in detail further on. The desired esters are generally obtained in the form of mixtures containing both cis- and trans-configuration isomers. When desired, the latter can then be separated from said mixtures by crystallization in appropriate solvents, wherein only one of the isomers is soluble.

Alternatively, the cis and trans isomers of these diesters can be obtained by esterification of the cis and trans isomers of the corresponding cyclohexanedicarboxylic acid. In the case of the 1,2- and 1,4-cyclohexanedicarboxylic acids for example, these isomers are commercial products.

The compounds (Ia) wherein the groups $R^1$ and $R^2$ are distinct can be obtained by transesterification of the above-mentioned symmetrical diesters, following known methods [see for example, K. Mori et al., Synth. 1973, 790]. The products of these transesterification reactions are mixtures of the starting symmetrical diesters with the corresponding asymmetrical diester and these two compounds are then separated by gas phase chromatography.

The other compounds (I) are also prepared by way of conventional reactions, illustrated in the following schemes:

of sodium chlorite—see J. March, Advanced Organic Chemistry, 3rd ed., p. 629, 1985).

I-General methods for preparing diesters (Ia)

A. Hydrogenation

A solution of the appropriate phenyl-dimethylcarboxylate (Fluka, 100 g, 0.51 mole) and of 5% Rh/C (2 g, Engelhard) in methanol (50 ml) was hydrogenated in an autoclave, at a temperature of 160° C. and $2\times10^7$ Pa hydrogen pressure. After filtration and concentration, the raw product was distilled (95° C./30 Pa) to provide the corresponding dimethyl cyclohexanedicarboxylate in essentially 100% yield.

B. Saponification

A solution of the dicarboxylate prepared under A. (25 g, 0.125 mole), NaOH (11 g, 0.275 mole) in water (300 ml) was taken to reflux during 5 h and then cooled down and acidified. The precipitate was filtered and washed with water to provide, after drying, the cyclohexanedicarboxylic acid Scheme II

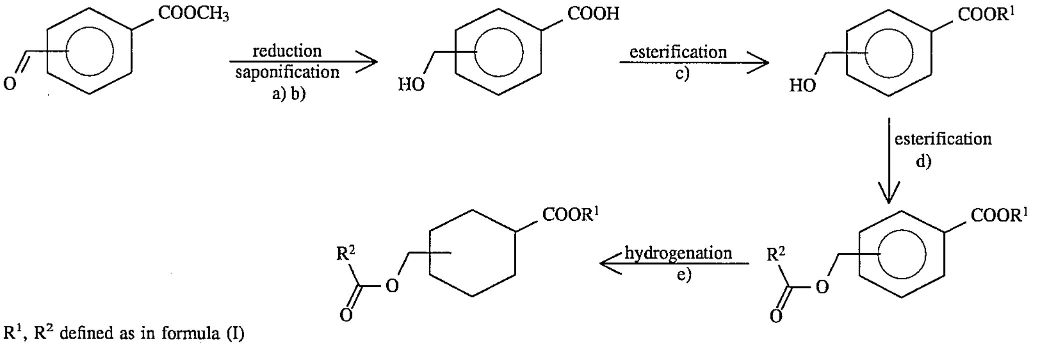

$R^1$, $R^2$ defined as in formula (I)
a) $NaBH_4$, methanol, ice bath
b) NaOH, water, reflux
c) $R^1OH$ (excess), conc. $H_2SO_4$, reflux
d) $R^2COCl$, toluene, pyridine
e) 5% Ru/Alox, ethyl acetate, $H_2$ The methyl formyl benzoates used as starting products in this reaction scheme are either commercial products, or they can be easily prepared by esterification of 2-, 3- or 4-carboxybenzaldehyde, the latter being commercially available compounds (from Aldrich, for example).

Scheme III

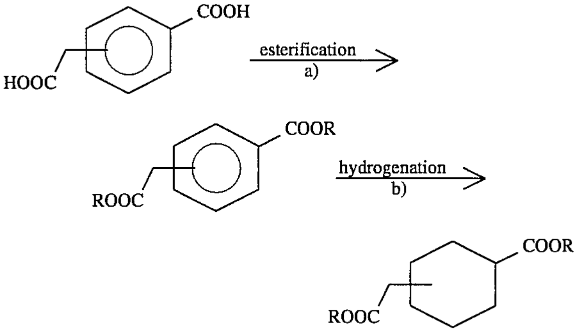

R = $C_1$-$C_4$ alkyl
a) $R^1OH$(excess), conc. $H_2SO_4$, reflux
b) 5% Ru/Alox, cyclohexane, $H_2$ The starting diacids in this scheme are either commercial products, as is the case of homophthalic acid, or they can be prepared via conventional oxidation of the commercially available carboxybenzaldehydes above-cited (i.e., by means corresponding to the starting diester, as a cis/trans isomer mixture.

C. Esterification

A solution of the acid prepared under B. (5 g, 29 mmole), $H_2SO_4$ conc. (2 ml) and appropriate ROH alcohol (R=$C_1$-$C_4$ alkyl; 50 ml), was refluxed during 5 h and then concentrated. The product was diluted in ether, washed with 5% NaOH and brine. Bulb-to-bulb distillation provided the corresponding dicarboxylate.

D. Transesterification

A mixture of the cyclohexanedicarboxylate obtained in A. or C., of the appropriate ROH alcohol and of catalytic amounts of KCN and $Na_2CO_3$ was heated to reflux. After the usual treatment, the reaction product was distilled. The asymmetric dicarboxylate and its symmetric homologue are then separated by gas phase chromatography. Thus, when we used for example dimethyl 1,4-cyclohexanedicarboxylate and propanol, we obtained as final products dipropyl 1,4-cyclohexanedicarboxylate and methyl propyl 1,4-cydohexanedicarboxylate.

In this way the following compounds (Ia) were prepared:

a. dimethyl 1,2-cyclohexanedicarboxylate

Prepared from 1,2-dimethylphthalate (Fluka) following method A.

The product obtained contained 80% of cis isomer and 20% of trans isomer.

Purity: 98%

B.p.: 95° C./30 Pa

NMR($^{13}$C): cis isomer: 42.7(d); 42.7(d); 26.3(t); 23.8(t); 23.8(t); 26.3(t) δ ppm trans isomer: 44.9(d); 44.9(d); 29.0(t); 25.3(t); 25.3(t); 29.0(t) δ ppm b. dimethyl 1,3-cyclohexanedicarboxylate Prepared by hydrogenation of 1,3-dimethylisophthalate (Fluka).

Cis/trans ratio: 63:37

B.p.: 102° C./15 Pa

NMR($^{13}$C): cis isomer: 42.5(d); 31.2(t); 42.5(d); 28.5(t); 24.9(t); 28.5(t) δ ppm trans isomer: 39.1(d); 29.5(t); 39.1(d); 28.0(t); 22.2(t); 28.0(t) δ ppm c. dimethyl 1,4-cyclohexanedicarboxylate Commercial origin product (Hüls; cis/trans mixture 2:1).

NMR($^{13}$C): cis isomer: 40.7(d); 26.1(t); 26.1(t); 40.7(d); 26.1(t); 26.1(t) δ ppm trans isomer: 42.4(d); 28.1(t); 28.1(t); 42.4(d); 28.1(t); 28.1(t) δ ppm d. diethyl 1,2-cyclohexanedicarboxylate Prepared by esterification of 1,2-cyclohexanedicarboxylic acid (cis/trans 86:14) by means of ethanol.

Cis/trans ratio: 86:14

Purity: 99%

B.p.: 110° C./10$^2$ Pa

NMR($^{13}$C): cis isomer: 42.7(d); 42.7(d); 26.3(t); 23.8(t); 23.8(t); 26.3(t) δ ppm trans isomer: 44.9(d); 44.9(d); 29.0(t); 25.3(t); 25.3(t); 23.0(t) δ ppm e. diethyl 1,3-cyclohexanedicarboxylate Prepared by esterification of 1,3-cyclohexanedicarboxylic acid (cis/trans 54:46).

Cis/trans ratio: 54:46

Purity: 99%

B.p.: 100° C./50 Pa

NMR($^{13}$C): cis isomer: 42.7(d); 31.1 (t); 42.7(d); 28.4(t); 24.9(t); 28.4(t) δ ppm trans isomer: 39.1(d); 29.3(t); 39.1(d); 27.9(t); 22.1(t); 27.9(t) δ ppm diethyl 1,4-cyclohexanedicarboxylate Prepared by transesterification of dimethyl 1,4-cyclohexanedicarboxylate. The reaction product was then subjected to gas phase preparative chromatography (3.5 m Carbowax 15%, He 30 m/min) to provide diethyl 1,4-cyclohexanedicarboxylate and methyl ethyl 1,4-cydohexanedicarboxylate.

diethyl 1,4-cyclohexanedicarboxylate:

Cis/trans ratio: 15:4

Purity: 99%

B.p.: 90° C./10 Pa

NMR($^{13}$C): cis isomer: 40.8(d); 26.1(t); 26.1(t); 40.8(d); 26.1(t); 26.1(t) δ ppm trans isomer: 42.6(d); 28.1(t); 28.1(t); 42.6(d); 28.1(t); 28.1(t) δ ppm methyl ethyl 1,4-cydohexanedicarboxylate:

Cis/trans ratio: 3:1

Purity: 98%

B.p.: 90° C./10 Pa

NMR($^{13}$C): cis isomer: 40.7(d); 26(t); 26(t); 40.7(d); 26(t); 26(t) δ ppm trans isomer: 42.4(d); 28.1(t); 28.1(t); 42.5(d); 28.1(t); 28.1(t) δ ppm Odor: floral, fruity.

g. dimethyl trans-1,4-cydohexanedicarboxylate and dimethyl cis-1,4-cyclohexanedicarboxylate Dimethyl 1,4-cyclohexanedicarboxylate (origin: Hüls; cis/trans ratio 2:1; half solid/half liquid product) was filtered in order to separate the mother liquors from the crystals. The latter (14.5 g) were taken in a mixture of 45 ml of 30°–50° petroleum ether and 7 ml of tert-butyl methyl ether and heat-crystallized. The crystals thus obtained (9.2 g) contained dimethyl trans-1,4-cyclohexanedicarboxylate (purity: 98%) having the following analytical characters:

M.p.: 68.1° C.

NMR($^1$H, 360 MHz): 3.67(s, 6H); 2.28(m, 2H); 2.05(m, 4H); 1.45(m, 4H) δ ppm

NMR($^{13}$C, 90 MHz): 175.9(2s); 51.6(2q); 42.4(2d); 28.1(4t) δ ppm

MS: 169(11), 168(30), 141(35), 140(94), 109(32), 108(46), 82(10), 81(100), 80(25), 79(22), 67(15), 59(20), 55(10)

To the mother liquors obtained after the above-mentioned filtration (92.0 g) there were added 22 ml of 30°–50° petroleum ether and the mixture was placed in the freezer. The crystals thus obtained (72.9 g) were distilled on a 15 cm Vigreux column (108° C./3×10$^2$ Pa) to provide 37.08 g of dimethyl cis-1,4-cyclohexanedicarboxylate (purity: 96%; cis/trans 75:25 mixture) having the following analytical characters:

NMR($^1$H, 360 MHz): 3.68(s, 6H); 2.48(m, 2H); 1.90(m, 4H); 1.68(m, 4H) δ ppm

NMR($^{13}$C, 90 MHz): 175.4(2s); 51.6(2q); 40.7(2d); 26.1(4t) δ ppm h. diethyl ci-1,4-cyclohexanedicarboxylate and diethyl trans-1,4-cyclohexanedicarboxylate These two compounds can be obtained by transesterification under soft-conditions [see for example, R. Imwinkelried and al., Org. Synth. 65, 230 (1987)] of the dimethyl cis- and trans-1,4-cyclohexanedicarboxylate described above. Alternatively, they can be prepared from cis- and trans-1,4-cyclohexanedicarboxylic acids, which are commercially available (Aldrich and Bader, for example) or can be easily prepared from the dimethyl dicarboxylates above-mentioned (saponification with NaOH in ethanol). According to this latter method, they were prepared as follows:

cis configuration isomer

A flask equipped with a water separator was charged with 4.17 g of cis-1,4-cyclohexanedicarboxylic acid (purity 87%; cis/trans 93:7), 3.35 g of ethanol, 3.71 g of isopropyl ether and 0.10 g p-toluenesulfonic acid, and the mixture was heated to reflux. After about 9 h of reaction, the mixture was poured on a decanter and washed with 10 ml of a solution saturated with $NaHCO_3$, two times with 10 ml of $H_2O$ and once with 5 ml of a solution saturated with NaCl. After drying over $Na_2SO_4$, filtration and concentration, the product was distilled on a 8 cm Vigreux column to provide a liquid product having the following analytical characters:

Purity: 93%

B.p.: 110° C./1.5×10$^2$ Pa

NMR($^1$H, 360 MHz): 4.14(q, J=8 Hz, 4H); 2.45(m, 2H); 1.90(m, 4H); 1.68(m, 4H); 1.26(t, J=8 Hz, 6H) δ ppm NMR($^{13}$C, 90 MHz): 175.0(2s); 60.2(2t); 40.8(2t); 20.1(4t); 14.3(2q) δ ppm MS: 228(M$^+$, 1), 183(29), 182(16), 155(29), 154(79), 109(48), 108(72), 82(10), 81(100), 80(42), 79(20), 67(20), 29(9)

trans configuration isomer

Prepared in an analogous manner to that of the previous compound but from the trans-1,4-cyclohexanedicarboxylic acid (98% pure). There is obtained a crystalline solid, which can be recrystallized from 30°–50° petroleum ether.

M.p.: 43.4° C.

Purity: 94%

NMR($^1$H, 360 MHz): 4.30(q, J=8 Hz, 4H); 2.26(m, 2H); 2.05(m, 4H); 1.46(m, 4H); 1.25(t, J=8 Hz, 6H) δ ppm NMR($^{13}$C, 90 MHz): 175.5(2s); 60.2(2t); 42.6(2d); 28.1(4t); 14.2(2q) δ ppm MS: 228(M$^+$, 1), 183(8), 182(21), 155(52), 154(100), 109(41), 108(39), 81(80), 79(20), 78(14), 67(12)

Other compounds prepared by the methods described included diisopropyl 1,2- and 1,3-cyclohexanedicarboxylates (cis/trans ratio 81:19, respectively 53:47), dipropyl 1,2-, 1,3- and 1,4-cydohexanedicarboxylates (cis/trans 86:14; 53:47; 4:3), dibutyl 1,4-cyclohexanedicarboxylate (cis/trans 3:1), methyl propyl 1,4-cyclohexanedicarboxylate (cis/trans 13:4) and methyl butyl 1,4-cydohexanedicarboxylate (cis/trans 90:10). All these compounds possessed floral, fruity type odors.

II-General methods for preparing the other diesters of the invention

A. According to scheme II

The conditions of the esterification, saponification or hydrogenation reactions indicated in this scheme were analogous to those already described above under I.

Step d) for obtaining alkoxides was carried out as follows: the compound obtained in step c) was dissolved in a mixture of pyridine and toluene and then the appropriate acyl chloride was added thereto dropwise, at about 40° C. After cooling, the mixture was poured on ice, taken in ether and the organic phase was washed to neutrality with a solution of HCl, $NaHCO_3$ and brine. The product was then purified by distillation.

The following compounds were thus prepared:

i. ethyl 4-(propanoyloxymethyl) benzoate (99% pure) NMR($^1H$, 360 MHz): 1.17(t, J=8, 3H); 1.39(t, J=7, 3H); 2.41(q, J=8, 2H); 4.38(q, J=7, 2H); 7.41(d, J=8, 2H); 8.02(d, J=8, 2H) δ ppm

MS: 236($M^+$, 26), 191(48), 180(74), 163(46), 107(100), 57(63), 29(41)

Odor: fruity, raspberry, slightly anis j. ethyl 4-(acetoxymethyl) benzoate (99% pure)

NMR(1H, 360 MHz): 1.39(t, J=7, 3H); 2.12(s, 3H); 4.38(q, J=7, 2H); 5.16(s, 2H); 7.41(d, J=8, 2H); 8.02(d, J=8, 2H) δ ppm

MS: 222($M^+$, 22), 180(71), 177(68), 107(100), 89(39), 43(53)

Odor: fruity, herbaceous k. methyl 4-(acetoxymethyl) benzoate (99% pure)

NMR ($^1H$, 360 MHz): 2.12(s, 3H); 3.92(s, 3H); 5.15(s, 2H); 7.4(d, J=8, 2H); 8.02(d, J=8, 2H) δ ppm

MS: 208($M^+$, 27), 177(36), 166(92), 133(42), 107(100), 89(47), 43(83)

Odor: slightly fruity, raspberry l. methyl 4-(propanoyloxymethyl)-1-cyclohexanecarboxylate (cis/trans 67:13, 90% pure)

NMR($^1H$, 360 MHz): 1.13(t, J=7, 3H); 2.32(q, J=7, 2H); 3.68(s, 3H); 3.93(d, J=7, 2H) δ ppm MS: (cis) 228($M^+$, 0), 197(2), 122(78), 94(100), 57(75), 29(29) (trans) 228($M^+$, 0), 197(4), 154(28), 122(72), 94(100), 57(82), 29(26)

Odor: fruity m. ethyl 4-(propanoyloxymethyl)-1-cyclohexanecarboxylate (cis/trans 33:7, 98% pure)

NMR(1H, 360 MHz): 1.13(t, J=8, 3H); 1.26(t, J=7, 3H); 2.41(q, J=8, 2H); 3.95(d, J=7, 2H); 4.14(q, J=7, 2H) δ ppm MS: (cis) 242($M^+$, 0), 213(1), 168(16), 141(32), 122(67), 94(100), 57(65), 29(42) (trans) 242($M^+$, 0), 168(28), 122(60), 95(93), 94(100), 57(74), 29(35)

Odor: described above n. ethyl 4-(acetoxymethyl)-1-cyclohexanecarboxylate (cis/trans 75:25, 98% pure)

NMR ($^1H$, 360 MHz): 1.26(t, J=7, 3H); 2.04(s, 3H); 3.93(d, J=7, 2H); 4.14(q, J=7, 2H) δ ppm MS: (cis) 228($M^+$, 0), 168(14), 141(37), 122(71), 94(100), 81(34), 43(71), 29(15) (trans) 228($M^+$, 0), 183(6), 168(20), 122(63), 95(100), 81(36), 43(67), 29(13)

Odor: fruity, add o. methyl 4-(acetoxymethyl)-1-cyclohexanecarboxylate (cis/trans 4:1, 98% pure)

NMR($^1H$, 360 MHz): 2.05(s, 3H); 3.68(s, 3H); 3.92(d, J=7, 2H) δ ppm

MS: (cis) 214($M^+$, 0),154(10), 141(20), 122(69), 94(94), 43(100) (trans) 214($M^+$, 0), 183(5), 154(20), 122(63), 81(52), 43(95)

Odor: fruity, powerful

B. According to scheme III

The reactions depicted in this scheme were carried out under analogous conditions to those already described.

Amongst others, the following compounds were prepared:

p. methyl 2-(methoxycarbonylmethyl)benzoate (95% pure)

NMR($^1H$, 360 MHz): 3.7(s, 3H); 3.87(s, 3H); 4.0(s, 2H); 7.22(d, J=8, 1H); 7.35(t, J=8, 1H); 7.47(t, J=8, 1H); 8.0(d, J=8, 1H) δ ppm

MS: 208($M^+$, 2), 176(88), 148(100), 133(94), 119(31), 91(65)

Odor: fruity q. propyl 2-(propoxycarbonylmethyl)benzoate (93% pure)

NMR($^1H$, 360 MHz): 0.90(t, J=7, 3H); 1.03(t, J=7, 3H); 1.62(q, J=7, 2H); 1.78(q, J=7, 2H); 4.01(s, 2H); 4.05(t, J=7, 2H); 4.23(t, J=7, 2H) δ ppm

MS: 264($M^+$, 1), 204(36), 162(100), 135(99), 118(34), 43(23)

Odor: fruity, phenolic, raspberry r. methyl 2-(methoxycarbonyl)-1-cyclohexaneacetate (cis/trans 1:1, 94% pure)

NMR($^1H$, 360 MHz): 3.66(s, 3H); 3.67(s, 3H) δ ppm MS: 214($M^+$, 0), 183(24), 154(55), 141(70), 114(54), 95(48), 81(100)

Odor: fruity, floral s. ethyl 2-(ethoxycarbonyl)-1-cyclohexaneacetate (94% pure)

NMR($^1H$, 360 MHz): 1.24(t, J=7, 3H); 1.25(t, J=7, 3H); 4.13(q, J=7, 2H); 4.14(q, J=7, 2H) δ ppm

MS: 242($M^+$, 0), 197(64), 168(67), 155(82), 128(68), 95(68), 81(100), 29(62)

Odor: fruity, slightly minty

The invention will now be described in greater detail by way of the following examples:

EXAMPLE 1

Composition parfumante

A base perfuming composition was prepared by admixing the following ingredients:

| Ingredients | Parts by weight |
|---|---|
| Synth. ambergris | 100 |
| Bergamot essential oil | 100 |
| Iralia ®[1)] | 100 |
| Musk ketone | 80 |
| 50% *Oakmoss absolute | 250 |
| Crystalmoss | 50 |
| Patchouli essential oil | 70 |
| Orange essential oil | 40 |
| Bourbon vetyver essential oil | 80 |
| Wardia ®[2)] | 80 |
| Total | 950 |

*in dipropyleneglycol (DIPG)

[1)]methylionone; origin: Firmenich SA, Geneva, Switzerland

[2)]rose type composition; origin: Firmenich SA, Geneva, Switzerland

To this base composition of the Chypre type there were added 50 parts by weight of diethyl 1,4-cyclohexanedicarboxylate to obtain a novel composition A, 50 parts by weight of Fructone® to obtain a composition B and 50 parts by weight of undecalactone to obtain a composition C. The latter then developed a Chypre type odor reminiscent of the fragrance of the perfume Femme® by Rochas. It possessed a very powerful and dominating lactonic note, with an alimentary character. Composition B developed a fruity, elegant note, but this fruity character had totally vanished 3 h later from the odor of a smelling strip which had been dipped in this composition.

Novel composition A possessed an even more elegant odor than that of composition B and less fruity-alimentary than that of composition C. Furthermore, its fruity, strawberry, pear character lasted all day long. These odor effects were even more marked when ethyl 1,4-cyclohexanedicarboxylate had been replaced by its pure cis configuration isomer.

EXAMPLE 2

Perfuming composition

A base perfuming composition was prepared by means of the following ingredients:

| Ingredients | Parts by weight |
|---|---|
| Benzyl acetate | 75 |
| Phenylethyl acetate | 75 |
| Bergamot essential oil | 50 |
| Citronellol | 185 |
| Geraniol | 200 |
| Linalol | 60 |
| Patchouli essential oil | 25 |
| Phenethylol | 260 |
| Rose absolute | 20 |
| Bulgarian rose essential oil | 10 |
| Total | 960 |

To this white rose type base composition there were added 40 parts by weight of diethyl 1,4-cyclohexanedicarboxylate (composition A) and 40 parts by weight of Fructone® (composition B). Novel composition A thus obtained had acquired a far more natural, fruity, ethereal odor than that of composition B, the latter possessing a more wine lees, alcoholic and fermented character. In addition, the fruity note of composition B had totally faded within 3 hours, whereas composition A had kept its fruity-ethereal character all day long.

EXAMPLE 3

Test of substantivity on linen

We prepared samples of perfumed detergent from an unperfumed detergent powder, to which there was added 0.1% by weight of respectively diethyl 1,4-cyclohexanedicarboxylate (sample A), Fructone® (sample B), hexyl acetate (sample C) and allyl caproate (sample D).

With these four detergent samples there were washed, in four separate washing machines, four standard textile batches. These four textile batches were afterwards evaluated on a blind test, both just out of the machine and after drying, by a panel of expert perfumers. The latter were asked to judge the strength of the fruity note developed by the textiles over time, by assigning an intensity value comprised within an increasing scale from 0 to 10.

The results of this blind evaluation are summarized in the following table:

| Washing sample | Textiles just out of the machine | Textiles after 0.5 h | 1 h | 1.5 h | 2 h | 3 h | 4 h | 6 h | 8 h |
|---|---|---|---|---|---|---|---|---|---|
| A | 8 | 7 | 6 | 5 | 4 | 4 | 4 | 2 | 1 |
| B | 6 | 5 | 4 | 3 | 2 | 2 | 1 | 0 | — |
| C | 10 | 5 | 0 | — | — | — | — | — | — |
| D | 9 | 5 | 2 | 0 | — | — | — | — | — |

These results clearly show that only the textiles washed with detergent sample A, which contained the compound of the invention, still developed a fruity odor after 4 h, which odor even lasted a few more hours, whereas all the other textiles had already become odorless.

What we claim is:

1. A perfuming composition or a perfumed article containing as an active perfuming ingredient diethyl 1,4-cyclohexanedicarboxylate.

2. The perfuming composition or perfumed article of claim 1, wherein diethyl 1,4-cyclohexanedicarboxylate is present in the form of its cis isomer or of a mixture containing a predominant amount of the cis isomer.

3. A perfume or cologne, a soap, a bath or shower gel, a shampoo or other hair-care product, a cosmetic preparation, a body deodorant, an air-freshener, a detergent, a fabric softener or a household product, which contains as a perfuming ingredient diethyl 1,4-cyclohexanedicarboxylate.

4. A method to impart, improve, enhance or modify the odor properties of a perfuming composition or of a perfumed article, which method comprises adding to said composition or article a fragrance effective amount of diethyl 1,4-cyclohexanedicarboxylate.

5. The method of claim 4, wherein diethyl 1,4-cyclohexanedicarboxylate is present in the form of its cis isomer or of a mixture containing a predominant amount of the cis isomer.

* * * * *